(12) United States Patent
Yanaihara et al.

(10) Patent No.: US 6,509,462 B2
(45) Date of Patent: Jan. 21, 2003

(54) ESTRADIOL DERIVATIVE AND IMMUNOASSY USING THE SAME

(75) Inventors: Noboru Yanaihara, Shizuoka (JP); Ikuo Kato, Fujinomiya (JP); Kazuyuki Kitamura, Fujinomiya (JP); Tsukasa Kodaira, Tokushima-ken (JP)

(73) Assignees: Otsuka Pharmaceutical Co., Ltd., Tokyo (JP); Yanaihara Institute, Inc., Shizuoka-ken (JP)

( * ) Notice: Subject to any disclaimer, the term of this patent is extended or adjusted under 35 U.S.C. 154(b) by 0 days.

(21) Appl. No.: 09/905,945

(22) Filed: Jul. 17, 2001

(65) Prior Publication Data

US 2002/0028929 A1 Mar. 7, 2002

(30) Foreign Application Priority Data

Jul. 18, 2000 (JP) ......................................... 2000-217314

(51) Int. Cl.[7] .......................... C07J 43/00; A61K 31/58; G01N 33/53; G01N 33/532
(52) U.S. Cl. ....................... 540/108; 540/108; 540/107; 514/169; 514/172; 514/176; 436/544; 436/811; 436/815; 436/817
(58) Field of Search ........................... 540/108; 514/172, 514/176; 436/544, 811, 815, 817

(56) References Cited

U.S. PATENT DOCUMENTS 5,342,760 A * 8/1994 Baker et al. ................ 435/7.92

OTHER PUBLICATIONS

Redeuilh et al. (DN 115:64884, CAPLUS, abstract of Methods of Enzymol. (1990, pp. 292–300), (Avid–Biotin Technol.).*
Majima et al. (AN 2002:639033, CAPLUS, abstract of Analytical Sciences (2002), 18(8), 869–874).*
Schwarz, S et al. (DN 131:286692, CAPLUS, abstract of Steroids (1999), 64(7), 460–471).*
Tiefenauer et al, *J. Steroid Biochem.*, 35 (6) : 633–639 (1990).
Meyer et al, *J. Steroid Biochem.*, 35 (2) : 263–269 (1990).
Bodmer et al, *J. Steroid Biochem.*, 33 (6) : 1161–1166 (1989).

* cited by examiner

Primary Examiner—Sabiha Qazi
(74) Attorney, Agent, or Firm—Sughrue Mion, PLLC

(57) ABSTRACT

The present invention provides a highly sensitive immunoassay system for estrogens, which utilizes as a labeled compound a biotinylated estradiol derivative of the formula (1)

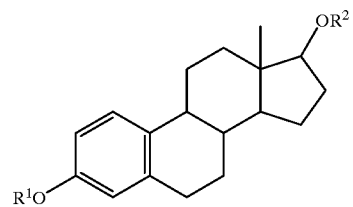

wherein one of $R^1$ and $R^2$ is hydrogen and the other is a group represented by

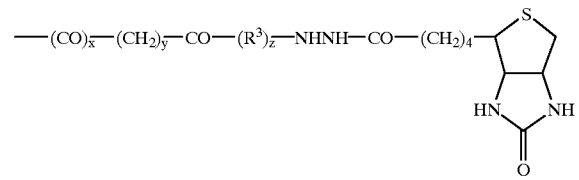

wherein $R^3$s are the same or different and represent an arginine residue or a lysine residue, x is 0 or 1, y is an integer from 1 to 5, and z is an integer from 1 to 3.

6 Claims, 6 Drawing Sheets

ESTRADIOL DERIVATIVE AND IMMUNOASSY USING THE SAME

FIELD OF THE INVENTION

The present invention relates to an immunoassay for estrogens, especially 17β-estradiol and estrone, and to a labeled compound used in the immunoassay.

BACKGROUND OF THE INVENTION

Estrogens are a representative example of steroid hormones (female sex hormones). Over ten kinds of compounds are currently known as estrogens. Estrogens are metabolized into stable estradiols in human blood like other female sex hormones. The estradiols are mainly excreted as urine and diffused into the environment such as into river water, lake water, seawater, waste water, soil, etc.

Estrogens have drawn attention because of the problem of feminization in humans, domestic animals, fish, etc. For example, 17-estradiol reacts with estrogen receptors. The avidity of the estradiol to the receptors is 1,000 to 10,000 times as high as the avidity of bisphenol A, nonylphenol, alkyl phthalates and the like which are now recognized as environmental hormones causing problems.

17β-estradiol and estrone have conventionally been measured by immunoassays such as radioimmunoassay and enzyme immunoassay. These immunoassays are known as techniques for measuring female sex hormones in human blood.

The immunoassays which were originally developed for the detection and measurement of female sex hormones in blood, however, remain unsatisfactory with respect to sensitivity, etc., when used for the detection and measurement of estrogens in environments such as river water, lake water, seawater, waste water and soil.

An object of the present invention is to solve the above problem of the prior art and provide a highly sensitive immunoassay system for estrogens.

SUMMARY OF THE INVENTION

The present inventors carried out intensive research and found that when a novel biotinylated estradiol derivative of the formula (1) shown below is utilized as a labeled compound in the immunoassay system for estrogens, a highly sensitive system for the detection and measurement of estrogens can be created. The present invention has been achieved based on this novel finding.

The present invention provides a biotinylated estradiol derivative represented by the formula (1)

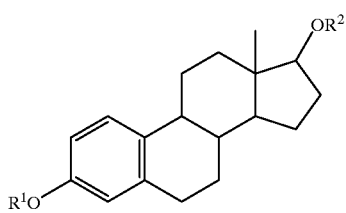

(1)

wherein one of $R^1$ and $R^2$ is an hydrogen atom and the other is a group represented by

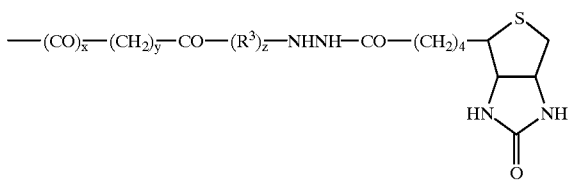

wherein $R^3$s are the same or different and represent an arginine residue or a lysine residue, x is 0 or 1, y is an integer from 1 to 5, and z is an integer from 1 to 3. The derivative represented by formula (1) is hereinafter referred to as "compound (1)".

Particularly, the present invention provides the biotinylated estradiol derivative wherein $R^1$ is a hydrogen atom, $R^3$ is an arginine residue, X is 1, Y is 2 and Z is 2, and the biotinylated estradiol derivative wherein $R^2$ is a hydrogen atom, $R^3$ is an arginine residue, X is 0, Y is 1, and Z is 2.

Further, the present invention provides an immunoassay system for estrogens which utilizes compound (1) as a labeled compound, particularly the immunoassay system for 17β-estradiol and estrone.

BRIEF DESCRIPTION OF THE DRAWINGS

In the specification, the accompanying drawings are referred to, wherein.

DETAILED DESCRIPTION OF THE INVENTION

Figure 1:
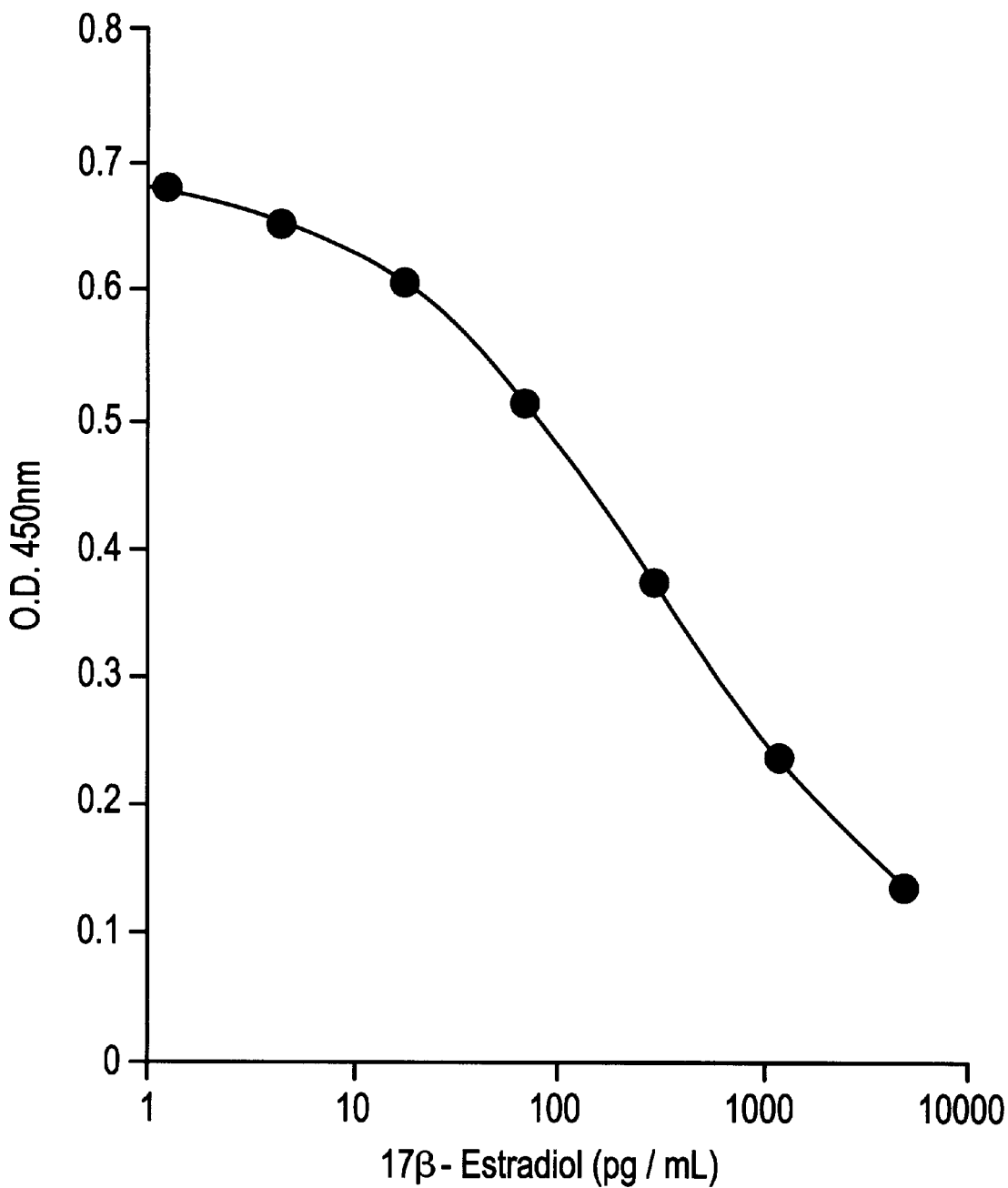
FIG. 1 is a standard curve obtained by an immunoassay of the invention as shown in Example 3-(1).

Compound (1) is soluble in a liquid phase used in an immunoassay system (it is water soluble). Therefore, compound (1) is highly useful as a labeled compound for estrogen immunoassay.

Conventionally, biotin has been used in combination with avidin as an indirect labeled compound. Biotin has a low molecular weight (molecular weight: 244.31) and is generally considered to be more suitable for use as a labeled compound, as compared with general enzymes. However, biotin is minimally soluble in water and a conjugate of biotin and minimally soluble estradiol is insoluble in water. Therefore, biotin can not be used for immunoassay of estrogens.

In contrast, compound (1) has the water-solubility necessary for estrogen immunoassay. Furthermore, compound (1) maintains cross-reactivity with the antibody used in the estrogen immunoassay system. Therefore, compound (1) is suitable for use in the estrogen immunoassay system. The development of such a compound has been desired in this field.

A preferred embodiment of the immunoassay method of the invention is an enzymatic immunoassay described in detail in Example 3 below. According to the preferred embodiment, levels of 17β-estradiol from about 1.2 to about 5000 pg/mL and levels of estrone from about 1.2 to about 20000 pg/mL are measurable.

As is clear from this data, the immunoassay system of the invention is a highly sensitive immunoassay system for the measurement of estrogens in the environment such as in river water, lake water and the like.

Compound (1) is advantageously used as a labeled compound in the immunoassay of estrogens, especially 17β-estradiol and estrone which are known to have high physiological activity.

In the formula (1) representing compound (1), the amino acid residues (Arg and Lys) represented by $R^3$ include D-isomers and L-isomers, unless otherwise specified.

Compound (1) can be produced via a condensation reaction between a compound of the formula (2) shown below (hereinafter referred to as compound (2)) and a compound of the formula (3) shown below (hereinafter referred to as compound (3)).

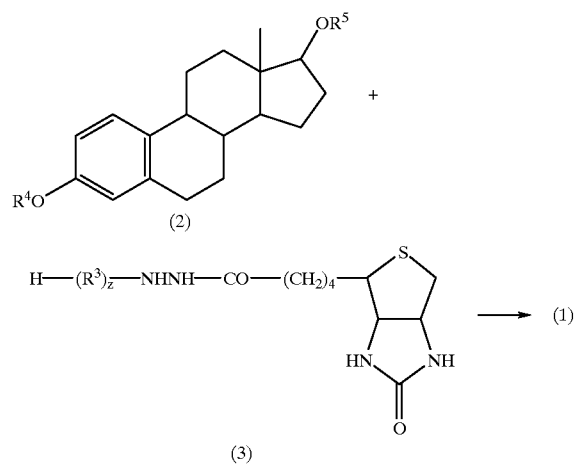

wherein one of $R^4$ and $R^5$ is hydrogen and the other is —(CO)$_x$—(CH$_2$)$_y$—COOH, and $R^3$, x, y and z are as defined above.

Compound (3) can be prepared by conventional methods for synthesizing peptides, for example, by condensing biotin hydrazide with one of the desired amino acids (when z is 1) or sequentially with two or more of the desired amino acids (when z is 2 or 3). The condensation reaction can be carried out by various known condensation methods. Such condensation methods include the commonly used liquid phase methods and solid phase methods.

Useful condensation methods include, for example, the azide method, mixed acid anhydride method, DCC method, activated ester method, oxidation-reduction method, DPPA (diphenylphosphoryl azide) method, DCC+additive method (additives: 1-hydroxybenzotriazole, N-hydroxysuccinimide, N-hydroxy-5-norbornene-2,3-dicarboximide, etc.), and Woodward method.

The solvent used in such condensation methods can be suitably selected from a variety of solvents conventionally used in such peptide condensation reactions. Examples of useful solvents include N-methylpyrrolidone (NMP), dimethylformamide (DMF), dimethylsulfoxide (DMSO) and a mixed solvent thereof.

The functional groups not involved in the condensation reaction can be protected with generally used protective groups according to conventional methods, and the protective groups can be removed after completion of the reaction. These reaction methods are known, and suitable reagents for use in these reactions may be selected from known ones.

Useful amino protective groups include benzyloxycarbonyl (Z), tertiary butoxycarbonyl (Boc), isobornyloxycarbonyl and p-methoxy benzyloxycarbonyl.

Useful carboxyl protective groups include, for example, groups capable of forming methyl ester, ethyl ester, tertiary butyl ester and like lower alkyl esters, benzyl ester or p-methoxybenzyl ester.

Useful guanidino protective groups of arginine include, for example, 2,2,5,7,8-pentamethylchromone-6-sulfonyl (Pmc), 2,2,4,6,7-pentamethyldihydrobenzofuran-5-sulfonyl (Pbf), nitro, Z, Boc, p-toluenesulfonyl and the like.

The protective group removal reaction can also be carried out by conventional methods such as catalytic reduction or methods using liquid ammonia and sodium, hydrogen fluoride, hydrogen bromide, hydrogen chloride, trifluoroacetic acid (TFA), acetic acid, methanesulfonic acid or the like.

Biotin hydrazide can be prepared by subjecting biotin and hydrazine protected by a suitable protective group such as Z, Boc or Troc (N-trichloroethoxycarbonyl) to a condensation reaction in the same manner as described above, followed by removal of the protective group from the resulting compound.

The condensation reaction between compound (3) and compound (2) can also be carried out in accordance with the above condensation reaction. The introduction and removal of protective groups may also be carried out as above.

The resulting compound (1) can be purified by a variety of conventional purification methods such as high performance liquid chromatography.

By using compound (1) in various immunoassays such as enzyme immunoassay (EIA), enzyme immunometric assay (ELISA), fluorescein immunoassay and luminescence immunoassay, estrogens, especially 17β-estradiol or estrone, can be detected and measured with high sensitivity.

The immunoassay of the invention essentially utilizes compound (1) as a labeled compound for the immunoassay system. In other respects, however, the immunoassay of the invention may be carried out in the same manner as usual immunoassay methods such as the competitive method or the sandwich method.

The antibody in the immunoassay system may be immobilized with a solid support and used. The solid support may be selected from a variety of solid supports conventionally used in the technical field. The method for immobilizing the antibody with the solid support is not particularly limited, either. The antibody can be immobilized by a physical bond or a chemical bond.

The immunoreaction in the immunoassay of the invention is not particularly limited and can be carried out under conditions usually used for immunoassays, generally at 45° C. or lower, usually at about 4 to about 40° C., for about 0.5 to several hours.

The reaction solvent and the pH of the reaction system are not particularly limited but should not adversely affect the reaction. Examples of useful solvents include citrate buffers, phosphate buffers, tris buffers and acetate buffers.

The immunoassay of the present invention is preferably carried out using a competitive method with compound (1) as a labeled compound, for example, in the following manner. First, an immobilized antibody for the target estrogen (immobilized anti-estrogen antibody) is prepared. In the presence of compound (1) as a labeled compound, a sample that may contain estrogens is added to the immobilized antibody, causing an antigen-antibody reaction (competition). Subsequently, the labeled compound bound to the immobilized antibody is measured using avidin as a detection reagent.

The avidin detection reagent is not particularly limited. For example, avidin or streptavidin modified with any labeling agent generally used in this field is usable.

The labeling agent is not particularly limited and may be selected from any known labeling agents. Preferable are enzymes such as alkaline phosphatase (ALP) and peroxidase (HRP). The modification of avidin with such a labeling agent can be carried out in accordance with known methods. The modified reagents are commercially available, also.

It is especially preferable that the immunoassay of the present invention be carried out in accordance with highly sensitive ELISA as described below in Examples.

The immunoassay of the invention according to a preferred embodiment includes an immunoassay for 17β-estradiol. In this method, compound (1) wherein $R^2$ is hydrogen is used as a labeled compound for the immunoassay system. An antibody reactive to 17β-estradiol is used as an estradiol-specific antibody in the immunoassay system. The antibody can be prepared using compound (2) wherein $R^5$ is hydrogen as an immunogen in accordance with the method described below.

The immunoassay of the invention according to another preferred embodiment includes an immunoassay for estrone. In this method, it is preferable that compound (1) wherein $R^1$ is hydrogen be used as a labeled compound for the immunoassay system. An antibody reactive to estrone is used as a specific antibody for the immunoassay system. The antibody can be prepared using compound (2) wherein $R^4$ is hydrogen as an immunogen in accordance with the method described below.

The immunoassay for estrogens of the invention can be expediently carried out by utilizing an immunoassay kit containing compound (1) as an active ingredient. The immunoassay kit may further contain other reagents necessary for the detection and measurement, such as the aforementioned avidin detection reagent, anti-estradiol antibody, standard antigen and assay buffer solution.

The immunoassay according to the invention is especially useful for the detection and measurement of estrogens in the environment such as in river water, lake water, sea water, waste water, soil and the like.

Further, the immunoassay according to the invention is useful for the detection and measurement of estrogens in organs, blood, urine or bone marrow of humans or other mammals, organs or blood of fish and the like.

Any antibody that specifically reacts with the target estrogen can be used as an anti-estrogen antibody in the immunoassay of the invention, and useful antibodies are not particularly limited in kind. Useful antibodies include the aforementioned antibodies or ones prepared in a similar manner. Specific examples include polyclonal antibodies such as antiserums of warm-blooded animals and chicken egg antibodies and monoclonal antibodies.

These antibodies can be selectively used depending on the estrogen to be measured. Preferred antibodies are, for example, antibodies reactive to 17β-estradiol and/or estrone.

The present inventors have confirmed that when low molecular weight organic compounds such as estrogens are used as antigens, the resulting polyclonal antibodies generally have a higher titer than the resulting monoclonal antibodies. Therefore, in the immunoassay of the present invention also, polyclonal antibodies are preferred.

Polyclonal antibodies are produced in the bodies of warm-blooded animals (except for humans) immunized against an antigen. The method or means for immunization can be carried out in a conventional manner.

Preferably used as the antigen is a conjugate of compound (2) and a carrier protein.

Any carrier protein known in the art as an enhancer for increasing immunogenicity of antigen or haptene can be used as the carrier protein. Examples of carrier proteins include albumin, globulin, thioglobulin, hemocyanin and like various animal proteins, polylysine and the like.

The conjugation reaction between compound (2) and the carrier protein can be carried out in a manner similar to the aforementioned condensation reaction. The reagent used for the reaction may also be a conventional one.

The conjugate of compound (2) and the carrier protein has the desired immunogenicity as it is and can be used as an antigen for producing an antibody suitable for use in the immunoassay of the invention.

The conjugate may further be adsorbed onto an appropriate polymer adsorbent and the resulting adsorbent may be used as an antigen.

The polymer adsorbent may be any of a variety of high molecular weight substances known in the art as enhancers for increasing immunogenicity. Specific examples include polyvinylpyrrolidone, latexes, porcine thioglobulin and like serum proteins, carbon powders and the like.

The desired adsorbent as an antigen can be prepared by blending such a polymer adsorbent with the conjugate in a conventional manner.

The immunization and the procedure for preparing the desired antibody may also be carried out in accordance with conventional methods. Polyclonal antibodies can be prepared, for example, in the following manner. An emulsion prepared by mixing the antigen with Freund's complete adjuvant is inoculated several times into a warm-blooded animal such as a rabbit, a sheep, a guinea pig, or a chicken to immunize the animal. Then the resultant antiserum is collected in a usual manner. When chickens are used, the desired polyclonal antibody can also be prepared by inoculating a hen with the antigen several times and producing eggs in which immunoglobulin (IgY) has been produced. Then IgY is isolated from the egg yolk in a usual manner.

Monoclonal antibodies may also be used as the antibody for the immunoassay of the invention. Monoclonal antibodies can be prepared, for example, in the following manner. Mice are inoculated several times with the antigen in combination with Freund's complete adjuvant, producing an antibody. Next, the resulting antibody-producing cells are fused with splenic cells or bone marrow cells using a conventional method such as the cell fusion method. Then the fused cells are cloned and the monoclonal cells which produce the desired antibody are isolated and cultured.

The antibodies thus obtained can be further purified according to conventional methods such as salting out using ammonium sulfate, ion exchange chromatography and affinity chromatography.

EXAMPLES

The present invention is described below in more detail with reference to Examples. It is to be understood that the invention is not limited to the embodiments described herein.

Example 1

Production Of Antibody (1) β-estradiol 3-carboxymethyl ether (6.3 mg 0.019 mmol; Sigma Co.) was dissolved in 100 μL of DMSO and 1 mL of 0.1 M PBS (pH 5.0). The solution was mixed with a solution of keyhole limpet hemocyanin (KLH; 20 mg; Pierce Chemical Company) in 1 mL of 0.1 M PBS (pH 5.0). Water-soluble carbodiimide (10 mg; Peptide Laboratory) was added and mixed. Next more water-soluble carbodiimide (178 mg) was added. The reaction was allowed to proceed at room temperature for 30 minutes.

The reaction mixture (2 mL) was mixed with 50% polyvinylpyrrolidone (2 mL; Merck & Co., Ltd.) and then Freund's adjuvant (4 mL; Calbiochem) was further added to form an emulsion.

The emulsion thus obtained was administered to three rabbits (Japan white, male, body weight: 2.0–2.5 kg) by subcutaneous injection in an amount of 2 mg of antigen per rabbit. For additional immunizations, a dose equal to half of that of the first immunization was administered 6 times at an interval of 2 weeks. One week after the final immunization, the rabbits were exsanguinated after confirming that their blood contained a sufficient titer of antiserum. The collected blood was allowed to stand at 37° C. for 1 hour and then at 4° C. overnight. The blood was centrifuged at 3000 rotation/minute and the resulting antiserum was lyophilized.

(2) Using βP-estradiol-17-succinic acid ester (6.3 mg; Sigma Co.), an emulsion was prepared in a similar manner as in (1) above. The emulsion was administered to three rabbits (Japan white, male, body weight: 2.0–2.5 kg) by subcutaneous injection in an amount of 1 mg of the antigen per rabbit, and the antiserum was obtained in a similar manner as in (1).

Example 2

Preparation Of Biotinylated Estradiol Derivative (1) Synthesis of Boc-Arg(Z)$_2$-NHNH-biotin (protective group Z: benzyloxycarbonyl)

Water soluble carbodiimide (212 μL, 1.2 mmol) was added dropwise to a DMF solution (10 mL) of Boc-Arg(Z)$_2$-OH (543 mg, 1.0 mmol), HOBt (162 mg, 1.2 mmol) and biotin-N$_2$H$_3$ (258 mg, 1.0 mmol) at −10° C. and stirred at room temperature for 18 hours. Then the solvent was distilled off. While the residue was cooled with ice, distilled water was added to solidify the residue. The precipitates were collected, followed by recrystallization from DMF-ethyl acetate to give 775 mg (99.1%) of Boc-Arg(Z)$_2$-CONHNH-biotin.

(2) Synthesis of Boc-Arg(Z)$_2$-Arg(Z)$_2$-NHNH-biotin
Boc-Arg(Z)$_2$-NHNH-biotin (352 mg, 0.45 mmol) prepared in (1) was dissolved in TFA (3 mL). The solution was stirred for 30 minutes, while it was cooled with ice. Then ester was added to remove the Boc. The resulting Boc-free product was subjected to a condensation reaction in DMF (5 mL), in a similar manner as above, using Boc-Arg(Z)$_2$-OH (293 mg, 0.54 mmol) and water-soluble carbodiimide (114 μL, 0.65 mmol) and HOBt (88 mg, 0.65 mmol). Then the solvent was distilled off. The reaction mixture was solidified by adding distilled water while the mixture was cooled with ice. The solid product was recrystallized from DMF-ethyl acetate to give 502 mg (92.4%) of the desired product.

(3) Synthesis of biotinylated estradiol derivative 1: compound (1) (wherein R$^1$=a hydrogen atom, R$^3$=an arginine residue, x=1, y=2 and z=2).

Boc-Arg(Z)$_2$-Arg(Z)$_2$-NHNH-biotin (65.2 mg, 0.054 mmol) prepared above in (2) was treated with TFA (0.5 mL) with ice-cooling for 30 minutes to remove the Boc. The resulting Boc-free product, in combination with β-estradiol-17-succinic acid ester (20.1 mg, 0.054 mmol) and HOBt (8.8 mg, 0.065 mmol), was dissolved in DMF (2 mL). Water-soluble carbodiimide (11.4 μL, 0.065 mmol) was added dropwise at −10° C. and stirred at room temperature for 18 hours. Then the solvent was distilled off. The residue was solidified by adding distilled water. The solid product was recrystallized from DMF-ethyl acetate to give 60 mg of the desired compound (Arg-protected compound).

The Arg-protected compound was catalytically reduced by hydrogen gas in the presence of 10%Pd-C (10 mg) in a mixed solvent of methanol (10 mL) and 50% acetic acid (10 mL) at room temperature for 4 hours. After removing the catalyst by filtration, the filtrate was lyophilized to give 40 mg of a crude product.

The crude product (40 mg) was dissolved in 50% acetic acid (2 mL) and purified by reversed-phase HPLC for preparative isolation through the column "YMC-PackD-ODS-5" (20×250 mm) using a 0.1% TFA/CH$_3$CN mixed solvent system as eluate (75/25→60/40; for 30 minutes) to give 26 mg of the desired compound.

Fab- mass spectrometry:

Anal. Calcd. for $(C_{44}H_{68}N_{12}O_8S+H)^+$: 925 Found: 925.168

(4) Synthesis of biotinylated estradiol derivative 2: compound (1) (wherein R$^2$=a hydrogen atom, R$^3$=an arginine residue, x=0, y=1 and z=2).

The biotinylated estradiol derivative 2 was synthesized in a similar manner as in (3). Stated more specifically, Boc-Arg(Z)$_2$-Arg(Z)$_2$-NHNH-biotin (20.4 mg, 0.019 mmol) was treated with TFA and condensed with β-estradiol-3-carboxymethyl ether (6.3 mg, 0.019 mmol) in DMF (1 mL) by the water-soluble carbodiimide and HOBt method. The post treatment was also carried out in a similar manner as above to give 21 mg of the desired compound (protected). The protected compound was catalytically reduced by hydrogen gas in the presence of 10%Pd-C (3 mg) in a mixed solvent of methanol (5 mL) and 50% acetic acid (5 mL) to give 14 mg of a crude product. The crude product (14 mg) was dissolved in 50% acetic acid (1.5 mL) and purified by reversed-phase HPLC for preparative isolation to give 3.5 mg of the desired compound.

Fab- mass spectrometry:

Anal. Calcd. for $(C_{42}H_{66}N_{12}O_7S+H)^+$: 883 Found: 883.133

Example 3

Immunoassay System (1) An ELISA system for 17β-estradiol using the derivative of the invention as a labeled compound was prepared in the following manner.

(1-1) Reagent and material:

<Assay buffer solution>

0.1% BSA-containing PBS(-)

<96 well plate>

Goat anti-rabbit IgG (Fc) immobilized onto a 96-well plate

<Labeled compound>

Biotinylated estradiol derivative 2 of the invention

<HRP-labeled reagent>

Streptavidin-HRP (Calbiochem Co.)

<Substrate>

TMB (Tetramethyl benzidine) solution (Sigma Co.)
<Antiserum>
RY725 (Rabbit antiserum obtained in Example 1-(1)
<Standard>
17β-estradiol (Sigma Co.)
<Wash solution>
0.05% Tween 20-containing physiological saline
<Enzyme reaction stop solution>
2N sulfuric acid (1-2) ELISA procedure:

(a) 100 μL of a standard solution or a sample is pipetted into each well of the 96-well plate, followed by addition of 50 μL of the labeled compound (0.2 ng/mL) comprising the biotinylated estradiol derivative of the invention and 50 μL of the antiserum (×32000);

(b) the reaction is allowed to proceed at 4° C. overnight (for 18–20 hours);

(c) all the wells are washed with the wash solution 4 times;

(d) the reaction is allowed to proceed using a microplate shaker at room temperature for 2 hours;

(e) all the wells are washed with the wash solution 4 times;

(f) 100 pL of the substrate is added;

(g) the reaction is allowed to proceed at room temperature for 20 minutes;

(h) 100 μL of the enzyme reaction stop solution is pipetted into each well;

(i) absorbance at 450 nm is measured with a microplate autoreader.

(1-3) Results

FIG. 1 shows a 17β-estradiol ELISA standard curve.

The result shown in FIG. 1 indicates that levels of 17β-estradiol from 1.2 to 5000 pg/mL are measurable with this system.

(2) An ELISA system for estrone using the derivative of the invention as a labeled compound was designed in the following manner.

(2-1) Reagent and material:
<Assay buffer solution>
0.1% BSA-containing PBS(-)
<96 well plate>
Goat anti-rabbit IgG (Fc) immobilized onto a 96-well plate
<Labeled compound>
Biotinylated estradiol derivative 1 of the invention
<HRP-labeled reagent>
Streptavidin-HRP (Calbiochem Co.)
<Substrate>
TMB (Tetramethyl benzidine) solution (Sigma Co.)
<Antiserum>
RY469 (Rabbit antiserum prepared in Example 1-(2)
<Standard>
Estrone (Sigma Co.)
<Wash solution>
0.05% Tween 20-containing physiological saline
<Enzyme reaction stop solution>
2N sulfuric acid (2-2) ELISA procedure:

(a) 100 μL of a standard solution or a sample is pipetted into each well of the 96-well plate, followed by addition of 50 μL of the labeled compound (0.25 ng/mL) comprising the biotinylated estradiol derivative of the invention and 50 μL of the antiserum (×32000);

(b) the reaction is allowed to proceed using a microplate shaker at room temperature for 5 hours;

(c) all the wells are washed with the wash solution 4 times;

(d) 100 μL of the HRP-labeled reagent (×5000) is added;

(e) the reaction is allowed to proceed using a microplate shaker at room temperature for 1 hour;

(f) all the wells are washed with the wash solution 4 times;

(g) 100 μL of the substrate is added;

(h) the reaction is allowed to proceed at 20° C. for 20 minutes;

(i) 100 μL of the enzyme reaction stop solution is pipetted into each well;

(j) absorbance at 450 nm is measured with a microplate autoreader.

(2-3) Results

Figure 2:
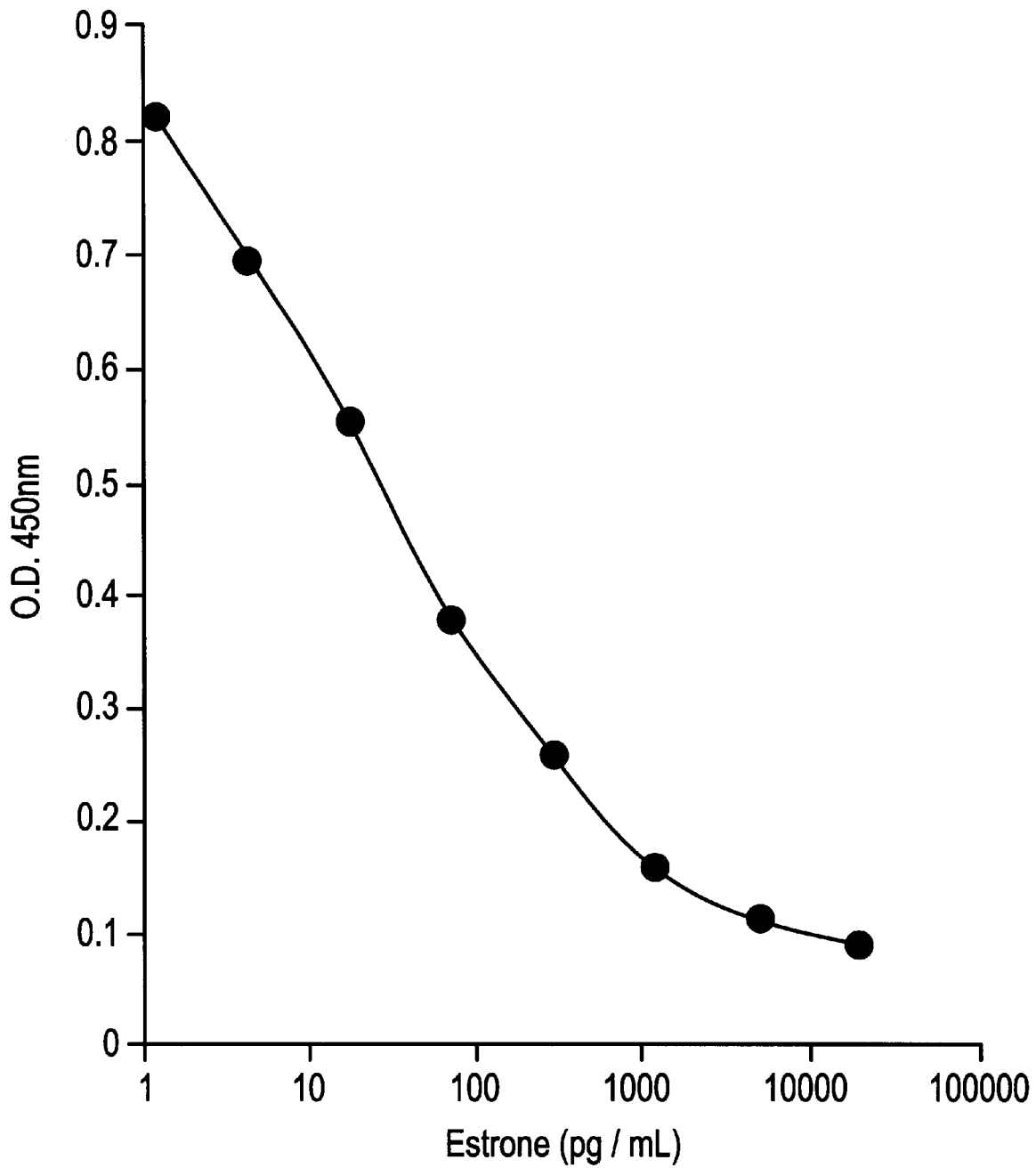
FIG. 2 is a standard curve obtained by an immunoassay of the invention as shown in Example 3-(2).

FIG. 2 shows an Estrone ELISA standard curve.

The result shown in FIG. 2 indicates that levels of estrone from 1.2 to 20000 pg/mL are measurable with this system.

Comparative Example 1

(1) The following ELISA system for 17β-estradiol was designed in a similar manner as in Example 3 (1), except that a commercially available labeled compound was used as a labeled compound for the system in place of the derivative of the invention.

(1-1) Reagent and material:
<Assay buffer solution>
0.1% BSA-containing PBS(-)
<96 well plate>
Goat anti-rabbit IgG (Fc) immobilized onto a 96-well plate
<Labeled compound>
Estradiol-HRP-labeled reagent (Estradiol-3-peroxidase labeled, Cosmo Bio Co.)
<Substrate>
TMB (Tetramethyl benzidine) solution (Sigma Co.)
<Antiserum>
RY725 (Rabbit antiserum obtained in Example 1-(l)
<Standard>
17β-estradiol (Sigma Co.)
<Wash solution>
0.05% Tween 20-containing physiological saline
<Enzyme reaction stop solution>
2N sulfuric acid (1-2) ELISA procedure:

(a) 100 μL of a standard solution or a sample is pipetted into each well of the 96-well plate, followed by addition of 50 μL of a labeled compound (×100) comprising the estradiol-HRP-labeled reagent and 50 uL of the antiserum (×8000);

(b) the reaction is allowed to proceed at 4° C. for overnight;

(c) all the wells are washed with the wash solution 4 times;

(d) 100 μL of the substrate is added;

(e) the reaction is allowed to proceed at room temperature for 30 minutes;

(f) 100 μL of the enzyme reaction stop solution is pipetted into each well;

(g) absorbance at 450 nm is measured with a microplate autoreader.

(1-3) Results

Figure 3:
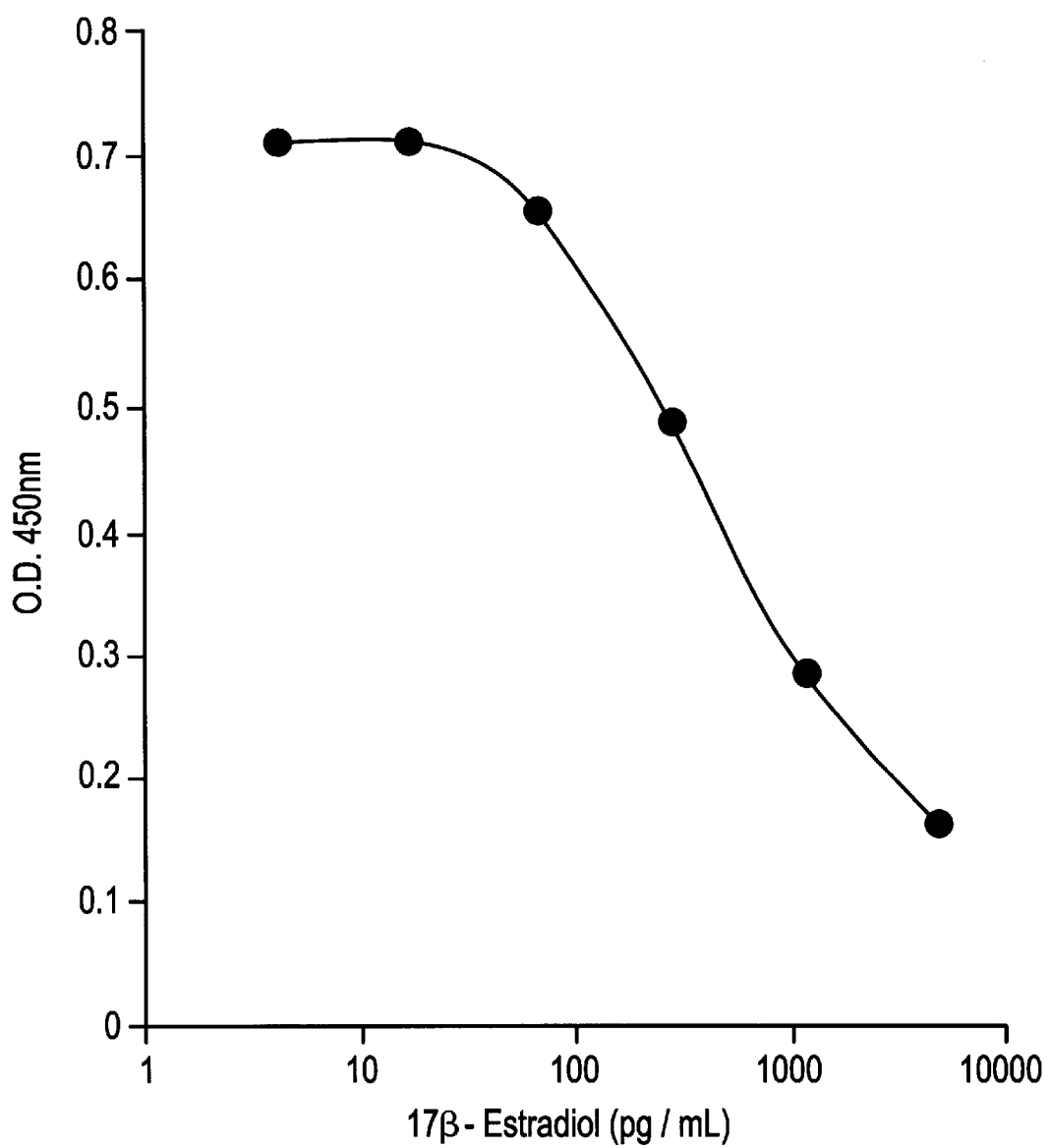
FIG. 3 is a standard curve obtained by a comparative immunoassay as shown in Comparative Example 1-(1).

FIG. 3 shows a 17β-estradiol ELISA standard curve.

The result shown in FIG. 3 indicates that levels of 17β-estradiol from 19.5 to 5000 pg/mL are measurable with this system.

(2) The following ELISA system for estrone was prepared in a similar manner as in Example 3-(2), except that a commercially available labeled compound was used as a labeled compound for the system in place of the derivative of the invention.

(2-1) Reagent and material:

<Assay buffer solution>

0.1% BSA-containing PBS(-)

<96 well plate>

Goat anti-rabbit IgG (Fc) immobilized onto a 96-well plate

<Labeled compound>

Estradiol HRP-labeled reagent (Estradiol-17-peroxidase labeled; Sigma Co.)

<Substrate>

TMB (Tetramethyl benzidine) solution (Sigma Co.)

<Antiserum>

RY469 (Rabbit antiserum obtained in Example 1-(2)

<Standard>

Estrone (Sigma Co.)

<Wash solution>

0.05% Tween 20-containing physiological saline

<Enzyme reaction stop solution>

2N sulfuric acid (2-2) ELISA procedure:

(a) 100 μL of a standard solution or a sample is pipetted into each well of the 96-well plate, followed by addition of 50 μL of a labeled compound (0.25 ng/mL) comprising the estradiol HRP-labeled reagent and 50 μL of the antiserum (×32000);

(b) the reaction is allowed to proceed using a microplate shaker at room temperature for 5 hours;

(c) all the wells are washed with the wash solution 4 times;

(d) 100 μL of HRP-labeled reagent (×5000) is added;

(e) the reaction is allowed to proceed using a microplate shaker at room temperature for 20 minutes;

(f) 100 μL of the enzyme reaction stop solution is pipetted into each well;

(g) absorbance at 450 nm is measured with a microplate autoreader.

(2-3) Results

Figure 4:
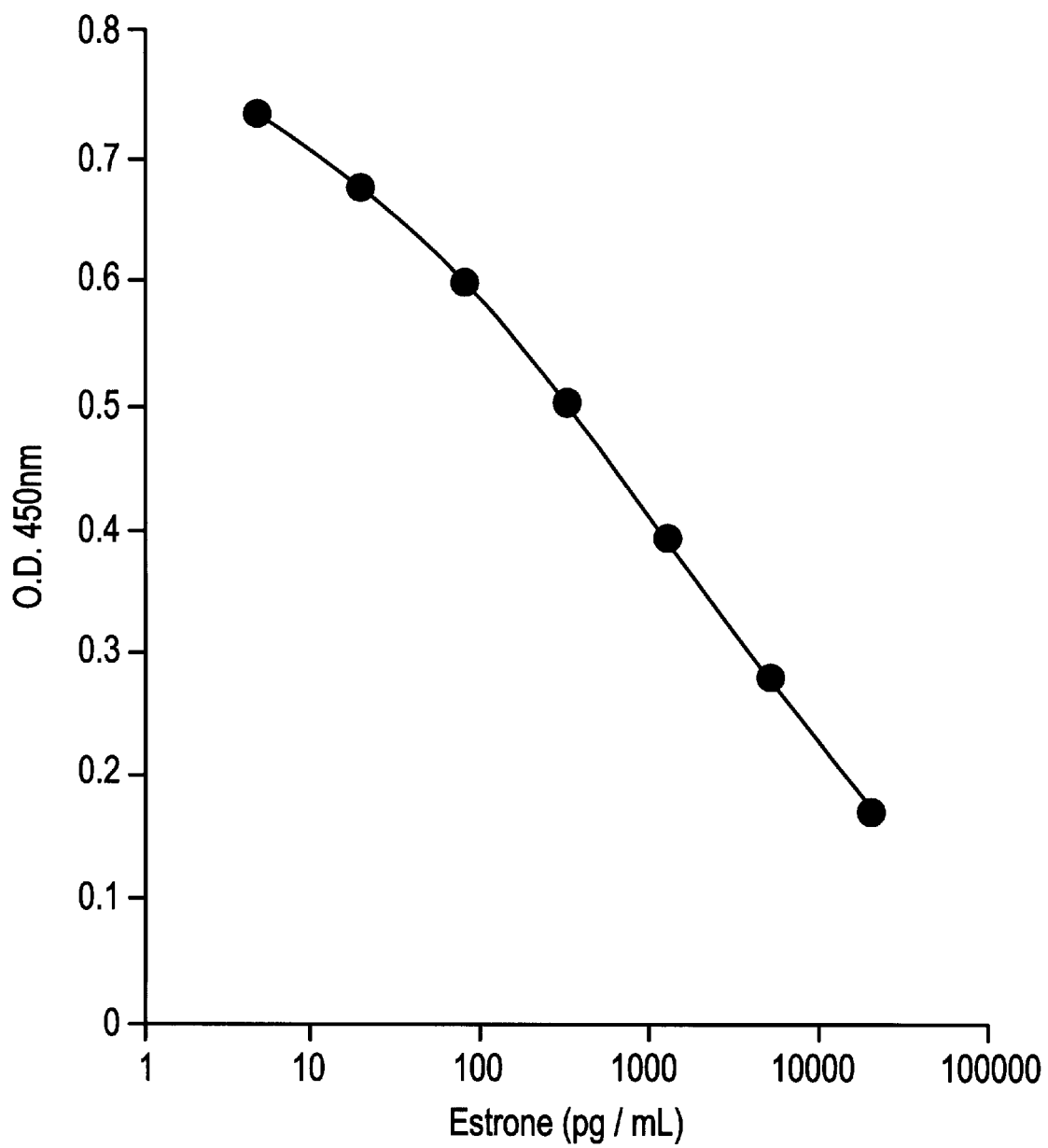
FIG. 4 is a standard curve obtained by a comparative immunoassay as shown in Comparative Example 1-(2).

FIG. 4 shows an estrone ELISA standard curve.

The result shown in FIG. 4 indicates that levels of estrone from 4.8 to 20000 pg/mL are measurable with this system.

Example 4

Cross-Reactivity Test Using ELISA System For 17β-Estradiol

The specifity of the 17β-estradiol ELISA system was assessed in the following manner.

Figure 5:
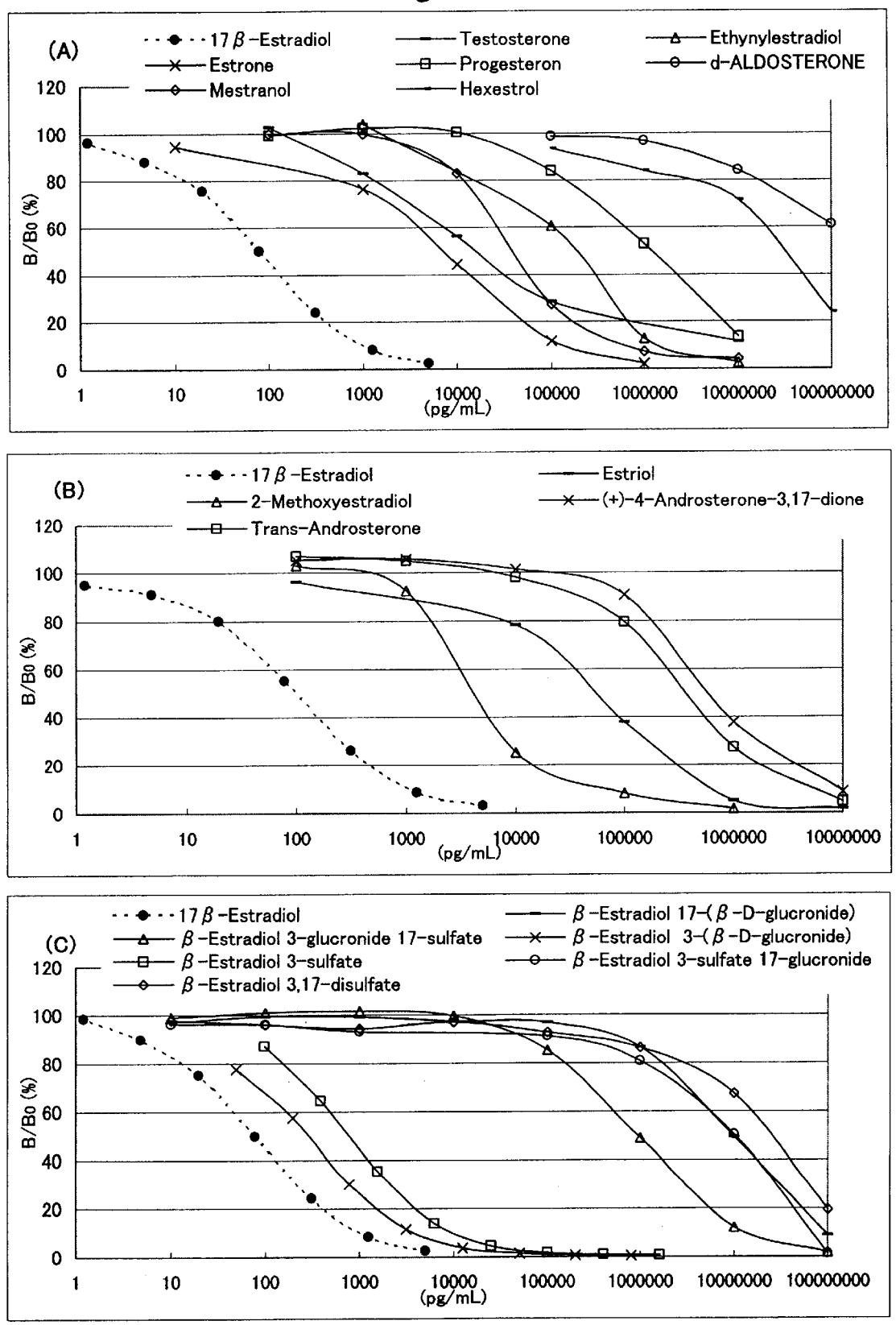
FIG. 5 is a graph showing the reactivity of the estrogens with the antiserum in the cross-reactivity test shown in Example 4.

ELISA was repeated in a similar manner as in Example 3-(1) except that the estrogens shown in Table 1 were used in place of the standard 17β-estradiol (Sigma Co.). The standard curve of each of the estrogens was obtained (see FIG. 5). The estrogen standard curves thus obtained and the 17β-estradiol standard curve obtained in Example 3-(1) were used to determine the cross-reactivity of the estrogens with the antiserum, relative to the cross-reactivity of 17β-estradiol (calculated as 100%). Table 1 shows the results.

TABLE 1

| Estrogen | Cross-reactivity (%) |
| --- | --- |
| 17β-Estradiol | 100.00 |
| Testosterone | 0.28 |
| Estrone | 0.94 |
| Progesteron | 0.01 |
| d-ALDOSTERONE | 0.00 |
| Estriol | 0.16 |
| (+)-4-Androsteron-3,17-dione | 0.02 |
| Trans-Androsterone | 0.02 |
| Mestranol | 0.14 |
| Ethynylestradiol | 0.03 |
| 2-Methoxyestradiol | 1.79 |
| Hexestrol | 0.00 |
| β-Estradiol 17-(β-D-glucronide) | 0.00 |
| β-Estradiol 3-glucronide 17-sulfate | 0.02 |
| β-Estradiol 3-(β-D-glucronide) | 37.44 |
| β-Estradiol 3-sulfate | 11.05 |
| β-Estradiol 3-sulfate 17-glucronide | 0.00 |
| β-Estradiol 3,7-disulfate | 0.00 |

Example 5

Cross-Reactivity Test Using ELISA System For Estrone

The specifity of the estrone ELISA system was assessed in the following manner.

Figure 6:
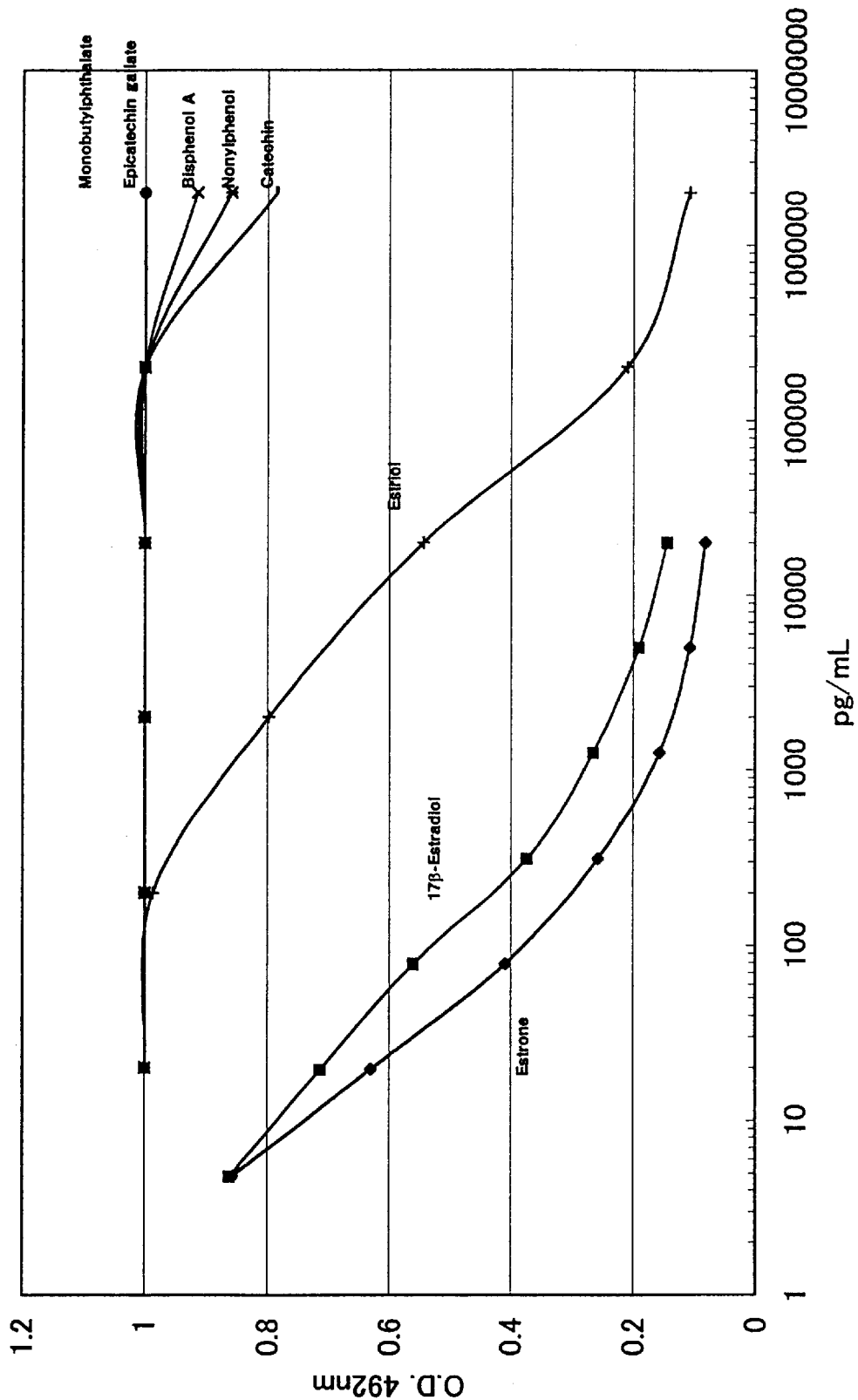
FIG. 6 is a g raph showing the reactivity of the estrogens with the antiserum in the cross-reactivity test shown in Example 5.

ELISA was repeated in a similar manner as in Example 3-(2) except that the estrogens shown in Table 2 were used in place of the standard estrone (Sigma Co.). The standard curve of each of the estrogens was obtained (see FIG. 6). The estrogen standard curves thus obtained and the estrone standard curve obtained in Example 3-(2) were used to determine the cross-reactivity of the estrogens with the antiserum, relative to the cross-reactivity of estrone (calculated as 100%) Table 2 shows the results.

TABLE 2

| Estrogen | Cross-reactivity (%) |
| --- | --- |
| Estrone | 100.00 |
| 17 β-Estradiol | 33.33 |
| Estriol | 0.15 |
| Bisphenol A | <0.001 |
| Nonylphenol | <0.001 |
| Monobutylphthalate | <0.001 |
| Catechin | <0.001 |
| Epicatechin gallate | <0.001 |

What is claimed is:

1. A biotinylated estradiol compound represented by the formula (1)

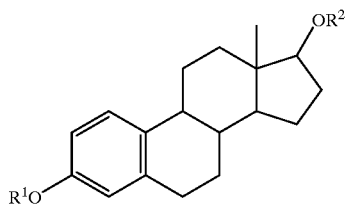

wherein one of $R^1$ and $R^2$ is a hydrogen atom and the other is a group represented by

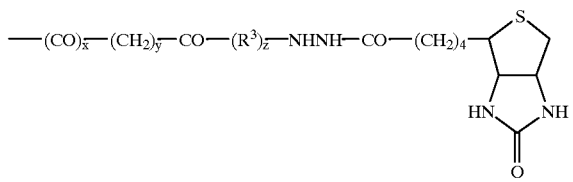

wherein $R^3$s are the same or different and represent an arginine residue or a lysine residue, x is 0 or 1, y is an integer from 1 to 5, and z is an integer from 1 to 3.

2. The biotinylated estradiol compound according to claim 1 wherein $R^1$ is a hydrogen atom, $R^3$ is an arginine residue, X is 1, Y is 2 and Z is 2.

3. The biotinylated estradiol compound according to claim 1 wherein R is a hydrogen atom, $R^3$ is an arginine residue, X is 0, Y is 1, and Z is 2.

4. An immunoassay system for estrogens which utilizes the biotinylated estradiol compound of claim 1 as a labeled compound.

5. The immunoassay system according to claim 4 which is a system for 17β-estradiol.

6. The immunoassay system according to claim 4 which is a system for estrone.

* * * * *